Figure 1A:
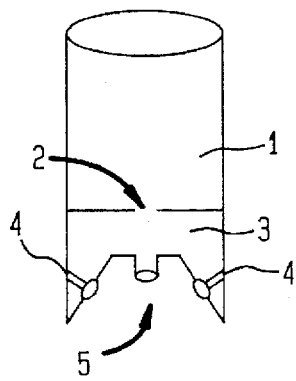
Figure 1B:
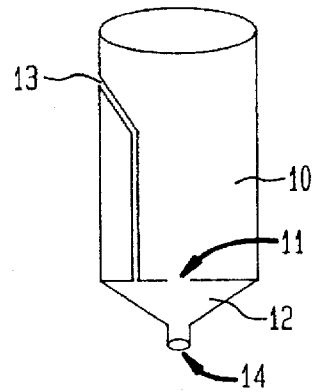

United States Patent [19]

McLaughlin

[11] Patent Number: 5,718,733
[45] Date of Patent: Feb. 17, 1998

[54] METHOD FOR ACCELERATING SOLIDIFICATION OF LOW MELTING POINT PRODUCTS

[75] Inventor: Adeline Frances McLaughlin, Southampton, N.J.

[73] Assignee: Rohm and Haas Company, Philadelphia, Pa.

[21] Appl. No.: 353,835

[22] Filed: Dec. 12, 1994

[51] Int. Cl.$^6$ .................. C07C 7/14; B01D 9/00
[52] U.S. Cl. .............. 23/295 R; 23/313 R; 264/13; 585/812; 585/816
[58] Field of Search ............. 23/313 R, 295 R; 264/12, 13; 585/812, 816

[56] References Cited

U.S. PATENT DOCUMENTS

| | | | |
|---|---|---|---|
| 2,656,396 | 10/1953 | Hayward | 264/13 |
| 3,231,413 | 1/1966 | Berquin | 23/313 R |
| 3,255,036 | 6/1966 | Kramer | 23/313 R |
| 3,579,721 | 5/1971 | Kaltenbach | 264/13 |
| 3,769,378 | 10/1973 | Young et al. | 264/13 |
| 3,771,929 | 11/1973 | Hellman et al. | 264/12 |
| 4,238,428 | 12/1980 | Sasaki et al. | 264/13 |
| 4,552,566 | 11/1985 | Kita et al. | 233/313 R |
| 4,818,279 | 4/1989 | Chaleat et al. | 264/13 |
| 5,236,466 | 8/1993 | Lauterback | 23/313 R |
| 5,435,945 | 7/1995 | DePaoli et al. | 264/13 |

FOREIGN PATENT DOCUMENTS

| | | | |
|---|---|---|---|
| 27228 | 8/1906 | Sweden | 23/313 R |
| 681609 | 9/1987 | U.S.S.R. | |
| 1640105 | 4/1991 | U.S.S.R. | 23/313 R |
| 1225116 | 3/1971 | United Kingdom | 23/313 R |

*Primary Examiner*—Gary P. Straub
*Attorney, Agent, or Firm*—Joseph F. Leightner

[57] ABSTRACT

A method for accelerating the solidification rate of low melting products is disclosed. The method of the invention comprises the atomization of a molten low-melting product within a fluid stream which greatly enhances the rate at which the low-melting product solidifies.

4 Claims, 1 Drawing Sheet

METHOD FOR ACCELERATING SOLIDIFICATION OF LOW MELTING POINT PRODUCTS

BACKGROUND OF THE INVENTION

This invention relates to a method for accelerating the solidification of low melting point products. More specifically this invention relates to a method for accelerating the solidification rate of low melting agrochemical products.

During the production and synthesis of many chemical products, a molten, viscous reaction product is obtained. In order to further process, react or package the reaction product, the molten product typically must be in a solid form. The rate at which the product solidifies is therefore very important in determining the rate at which product is produced. Unfortunately these molten, viscous products can take several days to solidify at room temperature.

Soviet Union Patent Application SU 681609, filed in 1986, discloses the accelerated crystallization of low melting pesticides by feeding a dispersed melt into a stream of particles flowing at a rate of 3–11 meters/second. While this method might accelerate the crystallization of the product, this procedure introduces an impurity, the particles, into the low melting point product.

Despite the teachings of the prior art, the solidification of molten products is still labor-intensive, time consuming and expensive. Accordingly, a need exists to provide a method to accelerate the solidification of low melting products without introduction of impurities or substrates.

SUMMARY OF THE INVENTION

The present invention provides a method for accelerating the solidification of low melting products which comprises providing a fluid stream; contacting the molten low melting product with the fluid stream such that the molten product is atomized; and collecting the atomized product. As used throughout the present application, "solidification time" is defined as the time necessary to form a sold material from the molten starting material. While the solidified product often forms a well defined crystalline structure, the term "solidified" as used throughout the specification also includes solidified materials in a non-crystalline structure.

It has been surprisingly found that the atomized product will solidify at an accelerated rate compared to products which have not been atomized. The method of the present invention is not dependent on the size of the sample, or the content of the fluid stream. Furthermore the atomization does not have to occur at elevated temperatures, unlike spray drying techniques. Unexpectedly it has also been found that the bulk density of the atomized material is similar to that obtained by conventional methods known in the art.

The method of the present invention can be applied to any low melting product which must be solidified. Suitable products include pharmaceuticals, agricultural products, biocides, dyes, organic chemicals and the like. Materials which can be used in the method of the present invention include myclobutanil; fenbuconazole; oxyfluorfen; isothiazolones such as 2-n-octyl-3-isothiazolone, 4,5-dichloro-2-n-octyl-3-isothiazolone, 2-methyl-3-isothiazolone and 5-chloro-2-methyl-3-isothiazolone; dithiopyr; thiazopyr; dicofol; and propanil.

As used throughout the application "low melting" is defined to be those products that have a melting point at a temperature below about 120° C., preferably those products that solidify from about 40° to about 100° C. and most preferably products that solidify from about 50° to about 90° C.

The product to be solidified is in a molten, highly viscous form and is pumped or otherwise fed under pressure to an atomization nozzle. Preferably the product is heated to reduce the viscosity of the product, preferably to a viscosity of less than about 100 centipoise. The atomization nozzle contains ports in which a fluid is provided to contact and atomize the molten product. The fluid must be provided in an amount sufficient to atomize the molten product.

The fluid to be used is not critical. Preferably the fluid is an inert gas for flammability considerations, however, non-inert gases may be employed. Suitable fluids include nitrogen, carbon dioxide, air, ethane, propane, steam, and mixtures thereof. Preferably the fluid is air or nitrogen, with nitrogen being most preferred.

The volume and pressure of the fluid which is to be delivered is dependent upon various factors including the weight and volume of product to be atomized and the configuration of the nozzle which is used to contact the gas and the product.

The fluid flow rate must be sufficient atomize the product provided at the nozzle. Generally the ratio of the flowrate of fluid to the flow rate of product must be greater than 0.4 standard cubic feet per minute of fluid per pound per minute of product. Preferably more than 2 and most preferably greater than 4 standard cubic feet per minute of fluid per pound per minute of product is provided to atomize the product.

One method of controlling product flowrates provided to the atomization nozzle is to vary the pressure within the product feed tank. Generally the pressure within the product holding tank must be greater than 5 psig to provide a sufficient flowrate of product to the atomization nozzle. Preferably the tank pressure is greater than 10 and most preferably from about 20 to about 55 psig. Other means for providing the molten product to the nozzle are known to those with skill in the art.

BRIEF DESCRIPTION OF THE DRAWING

FIGS. 1A and 1B show suitable nozzle designs for atomization, FIG. 2 shows a process flow diagram used to carry out the invention

DESCRIPTION OF THE PREFERRED EMBODIMENTS

Two possible nozzle designs are depicted in FIGS. 1*a* and 1*b*. FIG. 1*a* depicts an external nozzle design in which the fluid contacts the product external of the nozzle structure. The molten product flows through the entrance of the nozzle (1), through an orifice (2) to enter the fluid cap region (3). The fluid is provided through one or more orifices (4) such that the fluid contacts the molten product in an area external to the nozzle (5).

An internal nozzle design is depicted in FIG. 1*b*. The molten product is provided to the entrance of the nozzle (10) through an orifice (11) to enter the fluid cap region (12). The fluid is then provided through one or more orifices (13) to contact the molten product within the fluid cap region (12). The atomized product and fluid exit the internal nozzle design through exit aperture (14).

Both internal and external nozzle designs are available from Spraying Systems Company of Wheaton, Ill.

When an external nozzle is employed the flowrate of fluid and the flowrate of product are independent of one another. The flowrate of the fluid and the flowrate of the product can be independently set and the flowrates of the two streams do not have an effect on each other at the nozzle. When an internal nozzle is employed, the flowrate of the molten product is dependent on the gas flowrate available at the atomization nozzle. However, with an internal nozzle, the flow rate of the product and the gas flowrate at the nozzle are inversely related. Higher product flowrates at the nozzle reduces the fluid flowrate.

It has been discovered that the atomization pressure has a substantial impact on the time required to solidify the product. Generally, atomization pressures of less than about 6 pounds per square inch (psig) are insufficient for substantially reducing solidification times. Preferably atomization pressures of at least about 6 psig are employed and preferably the atomization gas pressure is greater than about 8 psig. Atomization gas pressures of from about 10 to about 20 psig are most preferred.

Figure 2:
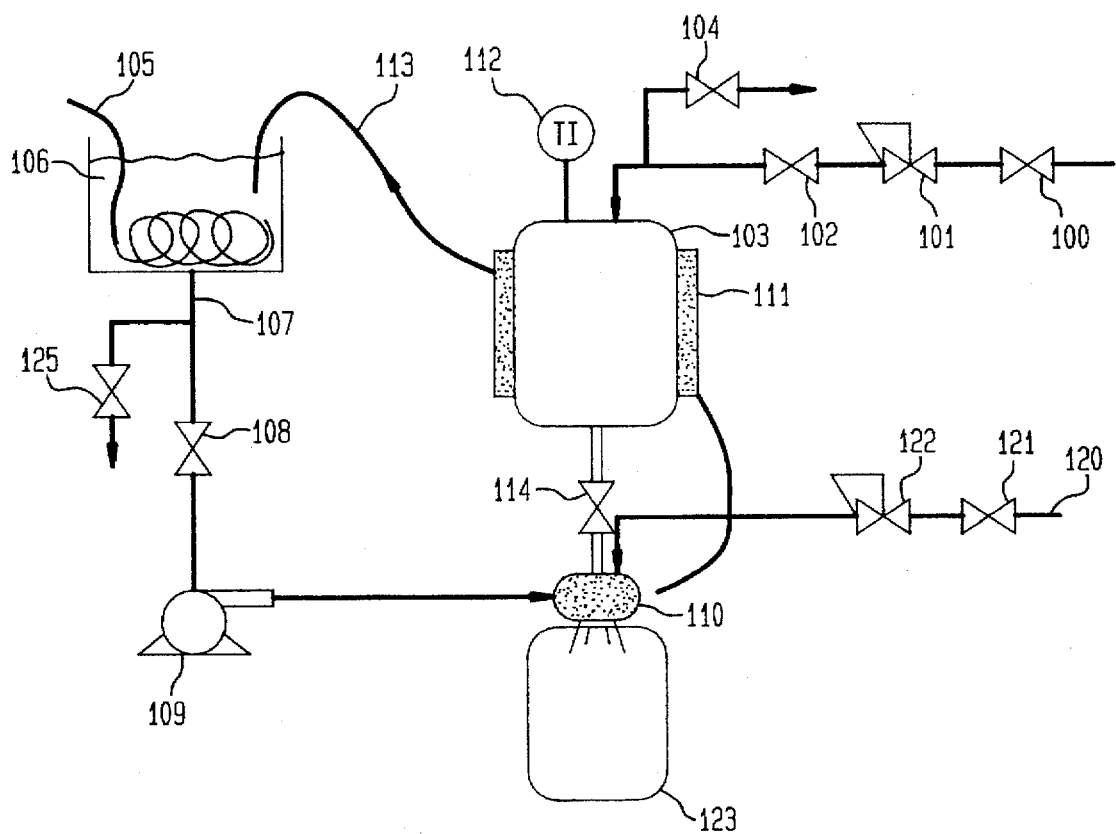

A process flow diagram of the apparatus used to carry out the present invention is depicted in FIG. 2. A pressurized fluid, such as nitrogen, is provided to the valve (100) to a pressure regulator (101) through a second valve (102) and into a jacketed feed tank (103). A vent valve (104) is normally closed during operation of the equipment. A heating source (105), such as steam, is provided to heat a heat transfer fluid, such as water in a heat transfer fluid tank (106). The steam may contact the water directly or a coil may be employed for providing the heat transfer. The heat transfer fluid is fed through line (107) through valve (108) to a circulation pump (109) to the jacket side (111) of the feed tank (103) to maintain the contents of the vessel at a substantially uniform temperature. The discharge valve (114) is opened when the feed tank is at the desired pressure and the molten product is delivered to the jacketed atomizing nozzle (110).

The atomizing fluid, such as nitrogen, is supplied through line (120) through valve (121) to a pressure regulator (122) and then to the atomizing nozzle (110). The atomized product is collected in a suitable collection device (123). The heat transfer fluid tank drain valve (125) is normally closed during operation of the system. The heat transfer fluid is supplied to a jacket around the nozzle (110) and then to the jacket (111) of the feed tank. A thermocouple (112) or other suitable temperature monitoring device is employed to maintain the contents of the feed tank at a constant temperature. The heat transfer fluid is returned to storage tank through line (113). For the sake of simplicity, all the piping and instrumentation necessary to operate the process is not depicted in FIG. 2. Piping and instrumentation modifications and other possible configurations of the process are known to those with skill in the art.

In addition to increasing the rate at which the product solidifies it has been surprisingly and unexpectedly been discovered that the bulk density of the product is not adversely effected. Previously, it was thought that atomization of the product would create hollow spaces within the solidified product thereby significantly reducing the bulk density of the product. Without wishing to be bound by any theory, the fluid is believed to accelerate the formation of initial crystal seed particles. The formation of the seed particle is thought to be similar to a rate determining step in a chemical reaction. Seed particles provide a nucleation site from which the product will quickly solidify. It is the formation of the seed particle which determines the rate of solidification.

In addition to accelerating the solidification of products, the present invention can also be used to deposit the atomized materials onto a carrier. Many chemical products are used when mixed with carriers such as clays, kaolin, silica, carbon black and the like. By atomizing the products directly onto a carrier the present invention can accelerate the solidification step and reduce the need for subsequent processing and handling.

EXAMPLE 1

Molten myclobutanil (technical grade) was heated to and maintained at about 90°–100° C. in a 2 gallon feed tank. At the outlet of the feed tank an external atomization nozzle with a nitrogen supply connected to it was provided. The feed tank was pressurized to 20 pounds per square inch (psig) to provide the myclobutanil concentrate to the nozzle. Nitrogen was also supplied at 10 psig through the nozzle. The atomized sample had completely solidified within 24 hours. A second sample of untreated myclobutanil concentrate required about 170 hours to solidify.

EXAMPLE 2

Oxyfluorfen (technical grade) was melted and maintained in a feed tank at 91° C. An internal atomization nozzle with a nitrogen source was provided at the outlet of the feed tank. The feed tank and oxyfluorfen contents were pressurized to 10 psig to deliver the oxyfluorfen to the atomization nozzle. Nitrogen was also supplied to the atomization nozzle at 12 psig. The oxyfluorfen was atomized by the nitrogen source and then collected. After two hours the atomized sample had completely solidified whereas after 2.5 hours a sample of the non-atomized oxyfluorfen was approximately 80% solidified.

EXAMPLE 3

The effect tank pressure and atomization pressure had on myclobutanil (technical grade) solidification was studied using equipment similar to that described in Example 1. Nitrogen was used to both pressurize the feed tank and to atomize the myclobutanil which was held at about 95° C. before atomization.

| Tank Pressure psig | Atomization Pressure psig | Solidification Time (hours to 100% solidification) |
|---|---|---|
| 10 | 2 | 170 |
| 10 | 6 | 170 |
| 10 | 10 | 20 |
| 10 | 14 | 20 |
| 20 | 2 | 95 |
| 20 | 6 | 95 |
| 20 | 10 | 20 |
| 20 | 14 | 18 |
| 55 | 2 | 95 |
| 55 | 4 | 95 |
| 55 | 10 | 20 |
| 55 | 14 | 20 |

Nitrogen atomization pressure had a significant effect on the time to complete solidification, with higher pressures enhancing the rate. The tank pressure had some effect on the solidification rate, but it is not as significant effect as the atomization pressure.

I claim:

1. A method for solidifying myclobutanil or oxyfluorfen consisting of:
   a) providing said myclobutanil or oxyfluorfen in molten form by heating;
   b) providing a stream of gas selected form the group consisting of nitrogen, carbon dioxide, air ethane, propane and mixtures thereof;
   c) concurrently contacting said myclobutanil or oxyfluorfen and gas stream such that the myclobutanil or oxyfluorfen is atomized in the gas stream in a downward direction and
   d) collecting the myclobutanil or oxyfluorfen as a melt and allowing the resulting melt of myclobutanil or oxyfluorfen to solidify.

2. The method of claim 1 wherein the gas stream is selected from the group consisting of: air, nitrogen and mixtures thereof.

3. The method of claim 1 wherein the gas stream is nitrogen.

4. The method of claim 1 wherein the step of providing the myclobutanil or oxyfluorfen in molten form comprising heating the myclobutanil or oxyfluorfen so that it has a viscosity of less than about 100 centipoise.

* * * * *